(12) United States Patent
Litz et al.

(10) Patent No.: US 7,989,580 B2
(45) Date of Patent: Aug. 2, 2011

(54) PHOSPHORESCENT IRIDIUM COMPLEXES

(75) Inventors: Kyle Erik Litz, Ballston Spa, NY (US); Kelly Scott Chichak, Clifton Park, NY (US); Donald Wayne Whisenhunt, Jr., Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 310 days.

(21) Appl. No.: 12/260,378

(22) Filed: Oct. 29, 2008

(65) Prior Publication Data

US 2010/0105852 A1    Apr. 29, 2010

(51) Int. Cl.
*C08G 79/00* (2006.01)
*C07F 15/00* (2006.01)
*C09K 11/06* (2006.01)
*C09K 11/08* (2006.01)

(52) U.S. Cl. ........ 528/395; 528/423; 556/136; 556/137; 556/138; 556/140; 548/402; 548/416; 548/560; 428/690; 428/689; 428/688; 428/917; 252/301.16; 252/301.35

(58) Field of Classification Search .................. 556/137, 556/136, 140; 528/395, 423
See application file for complete search history.

(56) References Cited

FOREIGN PATENT DOCUMENTS
WO    WO 2006/075905 A1 *   7/2006
WO    WO2008014037 A2      1/2008

OTHER PUBLICATIONS

Li et al., Huaxue Xuebao (Acta Chimica Sinica), 2008, 66(19), 2141-2145.*
PCT International Search Report dated Jan. 15, 2010.

* cited by examiner

*Primary Examiner* — Rip A. Lee
(74) *Attorney, Agent, or Firm* — Mary Louise Gioeni

(57) ABSTRACT

Metal complexes of formula I and IA and polymers derived from the complexes are useful in optoelectronic devices

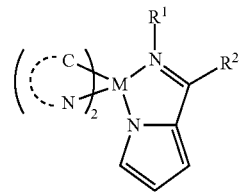

I

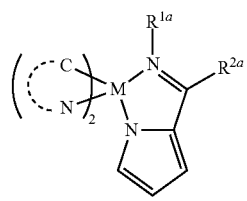

IA wherein
M is Ir, Co or Rh;

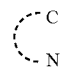

is a cyclometallated ligand;
$R^1$ is hydrogen, alkyl, substituted alkyl, aryl, substituted aryl, arylalkyl, or substituted arylalkyl;
$R^2$ is hydrogen, alkyl, substituted alkyl, aryl, substituted aryl, arylalkyl, substituted arylalkyl; and
at least one of $R^1$ and $R^2$ is other than hydrogen;
$R^{1a}$ is hydrogen, alkyl, substituted alkyl, aryl, substituted aryl, arylalkyl, or substituted arylalkyl;
$R^{2a}$ is hydrogen, alkyl, substituted alkyl, aryl, substituted aryl, arylalkyl, substituted arylalkyl;
and at least one of $R^{1a}$ and $R^{2a}$ is substituted alkyl, substituted aryl, substituted arylalkyl, and at least one substitutent of the substituted alkyl, substituted aryl, or substituted arylalkyl is a polymerizable group.

8 Claims, No Drawings

PHOSPHORESCENT IRIDIUM COMPLEXES

BACKGROUND

The invention relates generally to phosphorescent iridium complex(es), polymers that incorporate the complexes in a main chain or as end groups, and optoelectronic devices containing the complexes and polymers.

Organic light emitting devices (OLEDs), which make use of thin film materials that emit light when subjected to a voltage bias, are expected to become an increasingly popular form of flat panel lighting and display technology. This is because OLEDs have a wide variety of potential applications, including cellphones, personal digital assistants (PDAs), computer displays, informational displays in vehicles, television monitors, as well as light sources for general illumination. Due to their bright colors, wide viewing angle, compatibility with full motion video, broad temperature ranges, thin and conformable form factor, low power requirements and the potential for low cost manufacturing processes, OLEDs are seen as a future replacement technology for cathode ray tubes (CRTs) and liquid crystal displays (LCDs). Due to their high luminous efficiencies, OLEDs are seen as having the potential to replace incandescent, and perhaps even fluorescent, lamps for certain types of applications.

Light emission from OLEDs typically occurs via electrofluorescence, i.e. light emission from a singlet excited state formed by applying a voltage bias across a ground state electroluminescent material. It is believed that OLEDs capable of producing light by an alternate mechanism, electrophosphorescence, i.e. light emission from a triplet excited state formed by applying a voltage bias across a ground state electrofluorescecent material, will exhibit substantially higher quantum efficiencies than OLEDs that produce light primarily by electrofluorescence. Light emission from OLEDs by electrophosphorescence is limited since the triplet excited states in most light emitting organic materials are strongly disposed to non-radiative relaxation to the ground state. Thus, electrophosphorescent materials hold promise as key components of OLED devices and other optoelectronic devices exhibiting greater efficiencies relative to the current state of the art. For example, OLEDs capable of light production by electrophosphorescence are expected to exhibit a reduction (relative to OLEDs which produce light primarily by electrofluorescence) in the amount of energy lost to radiationless decay processes within the device thereby providing an additional measure of temperature control during operation of the OLED.

Improved light emission efficiencies have been achieved by incorporating a phosphorescent platinum-containing dye in an organic electroluminescent device such as an OLED (See Baldo et al., "Highly Efficient Phosphorescent Emission from Organic Electroluminescent Devices", Nature, vol. 395, 151-154, 1998) and phosphorescent iridium-containing dyes have also been employed (See for example Lecloux et al. United States Patent Application 20030096138, May 22, 2003). Notwithstanding earlier developments, there is currently considerable interest in finding novel phosphorescent materials which not only increase efficiency but also provide for a greater measure of control of the color of light produced by an OLED. For example, it would be highly desirable to provide novel phosphorescent materials which enable organic electroluminescent devices having improved overall efficiency, while at the same time allowing for the light output to be red shifted or blue shifted, depending on the nature of the application.

BRIEF DESCRIPTION

Briefly, in one aspect, the present invention relates to metal complexes of formula I, polymers derived from the complexes, and optoelectronic devices containing polymers derived from the complexes

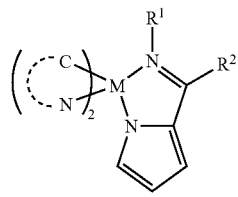

wherein

M is Ir, Co, or Rh;

is a cyclometallated ligand;

$R^1$ is hydrogen, alkyl, substituted alkyl, aryl, substituted aryl, arylalkyl, or substituted arylalkyl;

$R^2$ is hydrogen, alkyl, substituted alkyl, aryl, substituted aryl, arylalkyl, substituted arylalkyl; and at least one of $R^1$ and $R^2$ is other than hydrogen.

In particular embodiments, M may be Ir.

DETAILED DESCRIPTION

In the metal complexes of formula I, the cyclometallated ligand may be derived from phenylpyridine, difluoropyridine, tolylpyridine, benzothienylpyridine, fluorenylpyridine, thienylpyridine, benzothienylpyridine, 3-methoxy-2-phenylpyridine, thienylpyridine, phenylimine, vinylpyridine, pyridylnaphthalene, pyridylpyrrole, pyridylimidazole, phenylisoquinoline, dibenzoquinozaline, 8-hydroxyquinoline, ketopyrrole, picolinic acid, acetylacetone, hexafluoroacetylacetone, iminoacetone, 2-(1-naphthyl)benzoxazole)), 2-phenylbenzoxazole, 2-phenylbenzothiazole, salicylidene, salicylaldehyde, coumarin, phenylindole, derivatives thereof or combinations thereof. In particular, the cyclometallated ligand may be phenylpyridine or difluorophenylpyridine.

In particular embodiments, $R^2$ may be hydrogen. In some embodiments, $R^1$ may be substituted alkyl, substituted aryl, or substituted arylalkyl. A substitutent of the substituted alkyl, substituted aryl, or substituted arylalkyl may be a polymerizable group, particularly halo, hydroxyl, vinyl, allyl, vinyloxy, allyloxy, (meth)acrylate, alkylsiloxy, or a combination thereof. Particularly, $R^1$ may be substituted aryl.

In particular, $R^1$ may be selected from

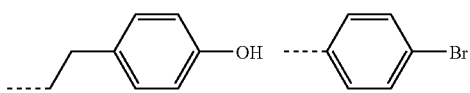

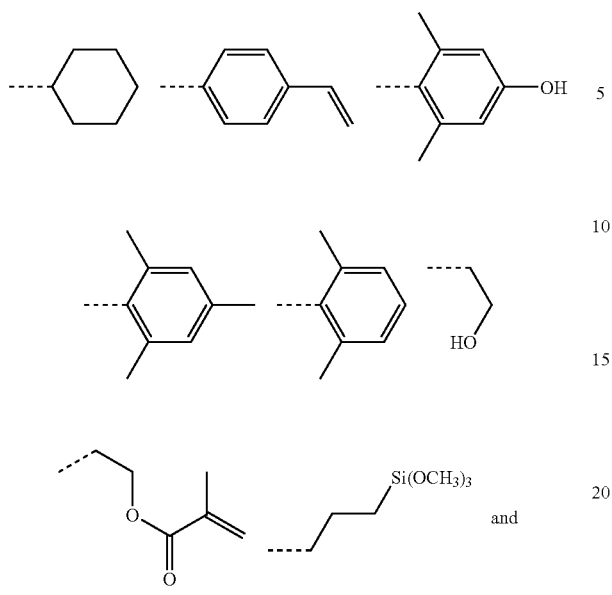
Particular examples of the metal complexes of the present invention include:
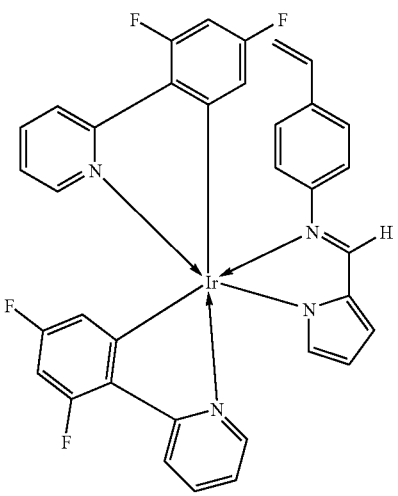

-continued

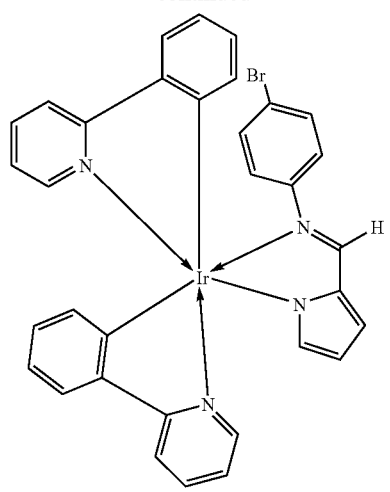

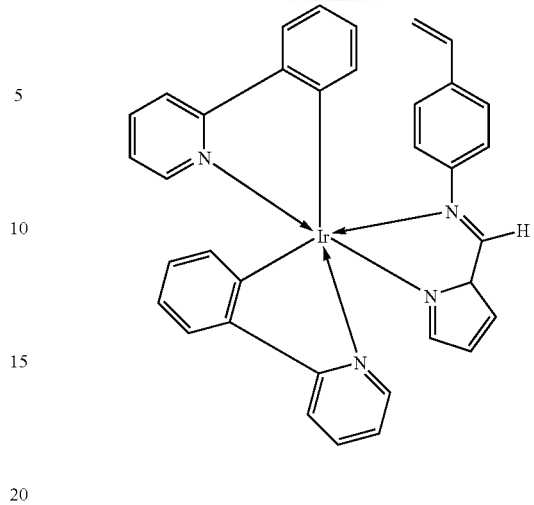

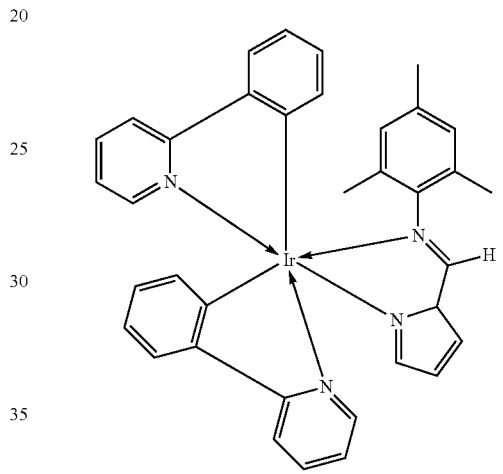

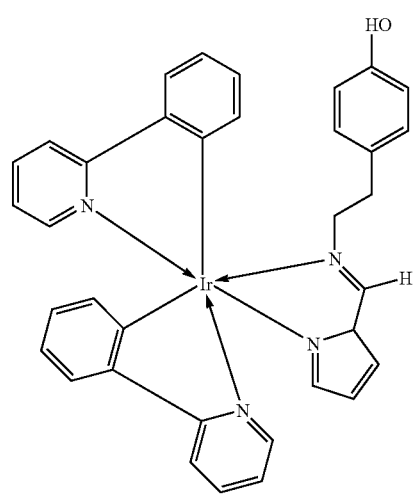

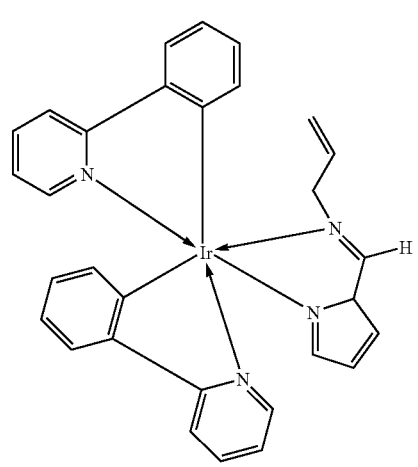

The optoelectronic devices according to the present invention include one or more polymers having structural or end units derived from the metal complex of formula I, that is, that incorporate the metal complex of formula I in the main chain or as end groups in the main chain or as end groups. The polymers are typically used in the light emitting layer. In particular, the optoelectronic devices may have at least one layer including a polymer having pendant groups or end groups derived from at least one metal complex of formula IA

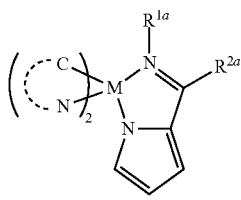

wherein M is as defined above;

is a cyclometallated ligand;
$R^{1a}$ is hydrogen, alkyl, substituted alkyl, aryl, substituted aryl, or arylalkyl, or substituted arylalkyl,
$R^{2a}$ is hydrogen, alkyl, substituted alkyl, aryl, substituted aryl, arylalkyl, or substituted arylalkyl; and
at least one of $R^{1a}$ and $R^{2a}$ is substituted alkyl, substituted aryl, substituted arylalkyl, and at least one substitutent of the substituted alkyl, substituted aryl, or substituted arylalkyl is a polymerizable group.

The polymers may include units in addition to those derived from the metal complexes of formula I, such as additionally include structural units derived from fluorene or substituted fluorene. Additional structural units may be derived from conjugated compounds, for example, those described in U.S. Pat. No. 6,900,285. In particular, structural units derived from tertiary aromatic amines may be used. The amount of structural units derived from unsaturated monomers ranges from about 0.05 mol % to about 50 mol %, particularly from about 1 mol % to about 25 mol %, and more particularly from about 1 mol % to about 10 mol %. In some embodiments, electroluminescent polymers such as poly(9,9-dioctyl fluorene) and copolymers thereof, such as F8-TFB may be blended with the polymers.

The polymers may be prepared by methods known in the art for making polyfluorenes, including Suzuki coupling of appropriate dihalo- and diboronate/diboronic acid-substituted monomers, and Yamamoto coupling. U.S. Pat. Nos. 5,708,130; 6,169,163; 6,512,083; and 6,900285 describe synthesis of polymers containing fluorene subunits.

An opto-electronic device, exemplified by an organic light emitting device, typically comprises multiple layers which include, in the simplest case, an anode layer and a corresponding cathode layer with an organic electroluminescent layer disposed between said anode and said cathode. When a voltage bias is applied across the electrodes, electrons are injected by the cathode into the electroluminescent layer while electrons are removed from (or "holes" are "injected" into) the electroluminescent layer from the anode. Light emission occurs as holes combine with electrons within the electroluminescent layer to form singlet or triplet excitons, light emission occurring as singlet excitons transfer energy to the environment by radiative decay. An opto-electronic device according to the present invention includes an organic electroluminescent layer composed of the polymer composition of the present invention.

Other components which may be present in an organic light-emitting device in addition to the anode, cathode and light emitting material include hole injection layers, electron injection layers, and electron transport layers. The electron transport layer need not be in contact with the cathode, and frequently the electron transport layer is not an efficient hole transporter and thus it serves to block holes migrating toward the cathode. During operation of an organic light-emitting device comprising an electron transport layer, the majority of charge carriers (i.e. holes and electrons) present in the electron transport layer are electrons and light emission can occur through recombination of holes and electrons present in the electron transport layer. Additional components which may be present in an organic light-emitting device include hole transport layers, hole transporting emission (emitting) layers and electron transporting emission (emitting) layers.

The organic electroluminescent layer is a layer within an organic light emitting device which when in operation contains a significant concentration of both electrons and holes and provides sites for exciton formation and light emission. A hole injection layer is a layer in contact with the anode which promotes the injection of holes from the anode into the interior layers of the OLED; and an electron injection layer is a layer in contact with the cathode that promotes the injection of electrons from the cathode into the OLED; an electron transport layer is a layer which facilitates conduction of electrons from cathode to a charge recombination site. A hole transport layer is a layer which when the OLED is in operation facilitates conduction of holes from the anode to charge recombination sites and which need not be in contact with the anode. A hole transporting emission layer is a layer in which when the OLED is in operation facilitates the conduction of holes to charge recombination sites, and in which the majority of charge carriers are holes, and in which emission occurs not only through recombination with residual electrons, but also through the transfer of energy from a charge recombination zone elsewhere in the device. A electron transporting emission layer is a layer in which when the OLED is in operation facilitates the conduction of electrons to charge recombination sites, and in which the majority of charge carriers are electrons, and in which emission occurs not only through recombination with residual holes, but also through the transfer of energy from a charge recombination zone elsewhere in the device.

Materials suitable for use as the anode include materials having a bulk conductivity of at least about 100 ohms per square, as measured by a four-point probe technique. Indium tin oxide (ITO) is frequently used as the anode because it is substantially transparent to light transmission and thus facilitates the escape of light emitted from electro-active organic layer. Other materials which may be utilized as the anode layer include tin oxide, indium oxide, zinc oxide, indium zinc oxide, zinc indium tin oxide, antimony oxide, and mixtures thereof.

Materials suitable for use as the cathode include zero valent metals which can inject negative charge carriers (electrons) into the inner layer(s) of the OLED. Various zero valent metals suitable for use as the cathode 20 include K, Li, Na, Cs, Mg, Ca, Sr, Ba, Al, Ag, Au, In, Sn, Zn, Zr, Sc, Y, elements of the lanthanide series, alloys thereof, and mixtures thereof. Suitable alloy materials for use as the cathode layer include Ag—Mg, Al—Li, In—Mg, Al—Ca, and Al—Au alloys. Layered non-alloy structures may also be employed in the cathode, such as a thin layer of a metal such as calcium, or a metal fluoride, such as LiF, covered by a thicker layer of a zero valent metal, such as aluminum or silver. In particular, the cathode may be composed of a single zero valent metal, and especially of aluminum metal.

Materials suitable for use in hole injection layers include 3,4-ethylenedioxythiophene (PEDOT) and blends of PEDOT with polystyrene sulfonate (PSS), commercially available from H.C. Stark, Inc. under the BAYTRON® tradename, and polymers based on the thieno[3,4b]thiophene (TT) monomer, commercially available from Air Products Corporation.

Materials suitable for use in hole transporting layers include 1,1-bis((di-4-tolylamino)phenyl)cyclohexane, N,N'-bis(4-methylphenyl)-N,N'-bis(4-ethylphenyl)-(1,1'-(3,3'-dimethyl)biphenyl)-4,4'-diamine, tetrakis-(3-methylphenyl)-N,N,N',N'-2,5-phenylenediamine, phenyl-4-N,N-diphenylaminostyrene, p-(diethylamino)benzaldehyde diphenylhydrazone, triphenylamine, 1-phenyl-3-(p-(diethylamino)styryl)-5-(p-(diethylamino)phenyl)pyrazoline, 1,2-trans-bis(9H-carbazol-9-yl)cyclobutane, N,N,N',N'-tetrakis (4-methylphenyl)-(1,1'-biphenyl)-4,4'-diamine, copper phthalocyanine, polyvinylcarbazole, (phenylmethyl)polysilane; poly(3,4-ethylendioxythiophene) (PEDOT), polyaniline, polyvinylcarbazole, triaryldiamine, tetraphenyldiamine, aromatic tertiary amines, hydrazone derivatives, carbazole derivatives, triazole derivatives, imidazole derivatives, oxadiazole derivatives having an amino group, and polythiophenes as disclosed in U.S. Pat. No. 6,023,371.

Materials suitable for use as the electron transport layer include poly(9,9-dioctyl fluorene), tris(8-hydroxyquinolato) aluminum (Alq3), 2,9-dimethyl-4,7-diphenyl-1,1-phenanthroline, 4,7-diphenyl-1,10-phenanthroline, 2-(4-biphenylyl)-5-(4-t-butylphenyl)-1,3,4-oxadiazole, 3-(4-biphenylyl)-4-phenyl-5-(4-t-butylphenyl)-1,2,4-triazole, 1,3,4-oxadiazole-containing polymers, 1,3,4-triazole-containing polymers, quinoxaline-containing polymers, and cyano-PPV.

EXAMPLES

Ligand Synthesis

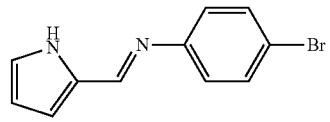

Example 1

An absolute ethanol (5 mL) solution of pyrrole-2-carboxaldehyde (Aldrich, 1.0 g, 10.51 mmoles) and 4-bromoaniline (Aldrich, 1.81 g, 10.52 mmoles) was prepared and mixed at 22° C. for 14 hours. The off-white solid precipitate that formed was collected by vacuum filtration (1.47 g, 6 mmoles, 56% yield). Analysis of the product by $^1$H— and $^{13}$C-NMR was consistent with the formation of the desired product, N-((1H-pyrrol-2-yl)methylene)-4-bromoaniline.

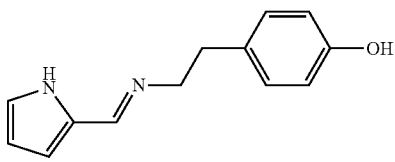

Example 2

An absolute ethanol (5 mL) solution of pyrrole-2-carboxaldehyde (Aldrich, 1.0 g, 10.51 mmoles) and tyramine (Aldrich, 1.44 g, 10.51 mmoles) was prepared and mixed at 22° C.

for 14 hours. The off-white solid precipitate that formed was collected by vacuum filtration (1.22 g, 5.7 mmoles, 54% yield). Analysis of the product by $^1$H— and $^{13}$C-NMR was consistent with the formation of the desired product, 4-(2-((1H-pyrrol-2-yl)methyleneamino)ethyl)phenol.

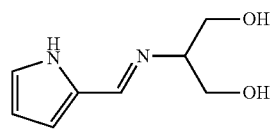

Example 3

An absolute ethanol (5 mL) solution of pyrrole-2-carboxaldehyde (Aldrich, 1.0 g, 10.51 mmoles) and serinol (Aldrich, 0.96 g, 10.51 mmoles) was prepared and mixed at 22° C. for 14 hours. Ethanol was removed by rotary evaporation leaving a light yellow oil product (1.2 g, 5.7 mmoles, 54% yield). Analysis of the product by 1H- and 13C-NMR was consistent with the formation of the desired imine.

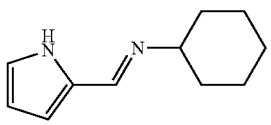

Example 4

An absolute ethanol (5 mL) solution of pyrrole-2-carboxaldehyde (Aldrich, 1.0 g, 10.51 mmoles) and cyclohexylamine (Aldrich, 1.04 g, 10.51 mmoles) was prepared and mixed at 22° C. for 14 hours. Ethanol was removed by rotary evaporation leaving a light yellow oil product (1.1 g, 5.7 mmoles, 54% yield). Analysis of the product by 1H- and 13C-NMR was consistent with the formation of the desired imine.

Example 5

An absolute ethanol (5 mL) solution of pyrrole-2-carboxaldehyde (Aldrich, 1.0 g, 10.51 mmoles) and ethanolamine hydrochloride (Aldrich, 1.03 g, 10.51 mmoles) was prepared and mixed at 22° C. for 14 hours. Ethanol was removed by rotary evaporation leaving a dark black oil product. Analysis of the product by $^1$H— and $^{13}$C-NMR was NOT consistent with the formation of the desired imine.

Combinatorial Synthesis of Ligands

General Method A

General procedure for imine ligand synthesis in ethanol: To different wells on the Chemspeed automated workstation was added 1.3 mmoles of the 6 amines listed below. Then 5 mL of dry ethanol was added under N$_2$. The reactor was then vortexed at 300 rpm at 25° C. for 10 minutes. A stock solution of 1H-pyrrole-2-carbaldehyde (1134 mg in 29.9 mL abs. EtOH) was placed on the Chemspeed automated workstation. The liquid handler of the Chemspeed automated workstation delivered 1.3 mmoles of 1H-pyrrole-2-carbaldehyde (~3.3 mL) to each well containing an amine. The vortex was increased to 850 rpm and the temperature increased to 75° C. for 10 hours. The vortex was then reduced to 300 rpm and the temperature decreased to 25° C.

General Method B

Using similar procedure to the one described above ~100 mg of activated 4A sieves, 1.3 mmoles of the 4 amines listed below and 5 mL of dry toluene were charged to different wells of the Chemspeed reactor. A stock solution of 1H-pyrrole-2-carbaldehyde (799 mg in 19.77 mL dry toluene) was placed on the Chemspeed automated workstation. The liquid handler of the Chemspeed automated workstation delivered 1.3 mmoles of 1H-pyrrole-2-carbaldehyde (~2.9 mL) to each well containing an amine. The vortex was increased to 850 rpm and the temperature increased to 75° C. for 10 hours. The vortex was then reduced to 300 rpm and the temperature decreased to 25° C.

Purification

Workup: For the imine ligands 4-((1H-pyrrol-2-yl)methyleneamino)-3,5-dimethylphenol and N-((1H-pyrrol-2-yl)methylene)-2,6-dimethylaniline it was determined that it was easiest to using the impure reaction mixtures in the next step so no further purification was done (for the toluene route the 4 Å sieves were removed by filtration). For the other ligands (independent of route) the solutions were filtered through 45 micron filters and the solvent removed under a stream on nitrogen. A small aliquot of ethanol was used to redissolved the residue and 1.5 g of silica gel was added to each reaction. The ethanol was removed under vacuum and the silica gels were used to load the Combi-flash chromatography system where the ligands were purified (Ethylacetate/hexane gradient). The fractions containing the product were combined and the solvent removed. The resulting solid was identified by NMR ($d_6$-DMSO).

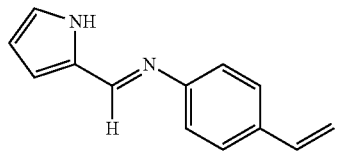

Example 6

Using general method B above, 4-vinylaniline was converted to N-((1H-pyrrol-2-yl) methylene)-4-vinylaniline.

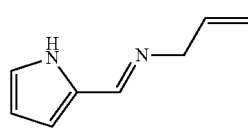

Example 7

Using general method B above, allylamine was converted to N-((1H-pyrrol-2-yl)methylene)prop-2-en-1-amine.

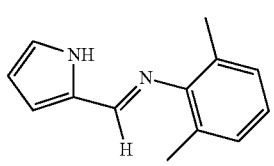

Example 8

Using general method B above, 2,6-dimethylaniline was converted to N-((1H-pyrrol-2-yl)methylene)-2,6-dimethylaniline.

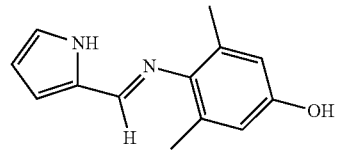

Example 9

Using general method B above, 4-amino-3,5-dimethylphenol was converted to 4-((1H-pyrrol-2-yl)methyleneamino)-3,5-dimethylphenol.

Synthesis of Phosphorescent Complexes

Example 10

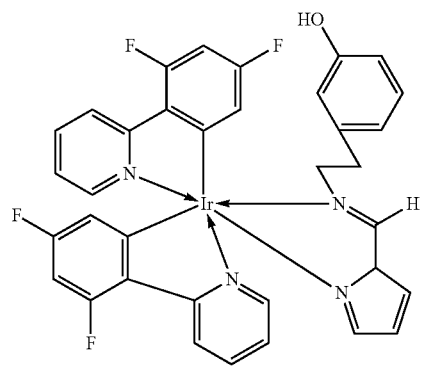

[(4,6-difluorophenyl)-pyridinato-N,$C^2$]$_2$IrCl dimer (American Dye Source, 0.25 g, 0.20 mmoles) was dissolved in 6 mL dimethylformamide containing 4-(2-((1H-pyrrol-2-yl)methyleneamino)ethyl)phenol (Example 2, 0.102 g, 0.48 mmoles) and sodium carbonate (Aldrich, 0.25 g, excess). The solution was heated to 85° C. for 14 hours. The solution was cooled to 22° C. and filtered to separate from sodium carbonate. Dropwise addition into hexanes produced a yellow microcrystalline solid (170 mg, 53% yield). The structure was confirmed by $^1$H— and $^{13}$C-NMR.

Example 11

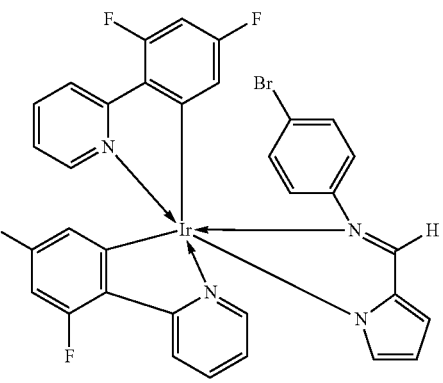

[(4,6-difluorophenyl)-pyridinato-N,C$^2$]$_2$IrCl dimer (American Dye Source, 0.25 g, 0.20 mmoles) was dissolved in 6 mL dimethylformamide containing N-((1H-pyrrol-2-yl)methylene)-4-bromoaniline (Example 1, 0.130 g, 0.48 mmoles) and sodium carbonate (Aldrich, 0.25 g, excess). The solution was heated to 85° C. for 14 hours. The solution was cooled to 22° C. and filtered to separate from sodium carbonate. Dropwise addition into hexanes produced a yellow microcrystalline solid (194 mg, 58% yield). The structure was confirmed by $^1$H— and $^{13}$C-NMR.

Combinatorial Synthesis of Phosphorescent Complexes

General Method C: The ligands of Examples 6-9 above were reacted independently with two Ir complexes [(4,6-F$_2$ppy)$_2$IrCl]$_2$ and [(ppy)$_2$IrCl]$_2$ in THF/toluene using the following procedure: each ligand (300 □moles) either as a solid or in a toluene solution was charged to a Chemspeed reactor with 220 mg of Na$_2$CO$_3$. Toluene was added to bring the total volume to 5 mL. The Ir dimers were added as slurries from THF (100 □moles of dimer). THF was added to bring the total volume to 10 mL. The chemspeed reactors were vortexed at 850 rpm for 14 hours at 85° C. The solutions were then filtered through 45 micron filters and washed with THF. The THF was removed and the residue redissolved in a minimum of THF. Silica gel (1.5 g) was then added and the THF removed under vacuum. The silica gels were used to load the Combiflash chromatography system where the complexes (see below) were purified (ethylacetate/hexanes gradient). The fractions containing the product were combined and the solvent removed. The residues were recrystallized from chloroform/hexanes and the products identified by NMR spectroscopy.

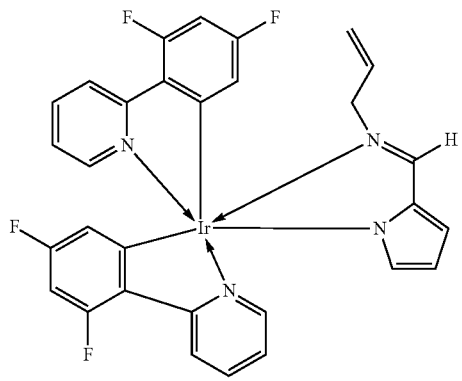

Example 12

According to General Method C above, reaction of N-((1H-pyrrol-2-yl)methylene)prop-2-en-1-amine (Ex 7) with [(4,6-difluorophenyl)-pyridinato-N,C$^2$]$_2$IrCl dimer gave the desired product (83 mg, 59% yield).

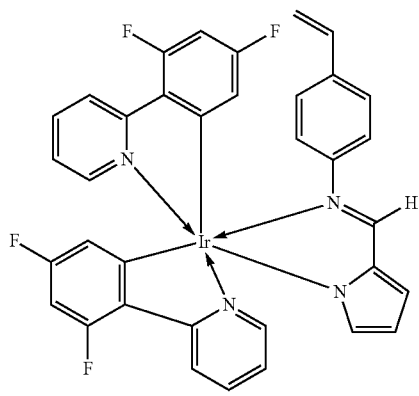

Example 13

According to General Method C above, reaction of N-((1H-pyrrol-2-yl)methylene)-4-vinylaniline (Ex 6) with [(4,6-difluorophenyl)-pyridinato-N,C$^2$]$_2$IrCl dimer gave the desired product (89 mg, 58% yield).

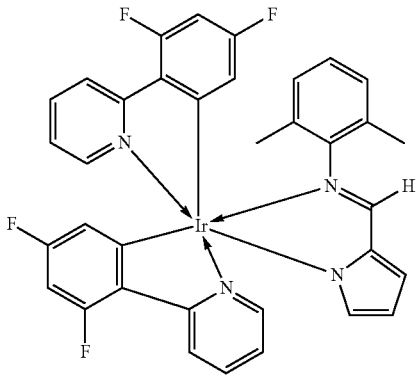

Example 14

According to General Method C above, reaction of N-((1H-pyrrol-2-yl)methylene)-2,6-dimethylaniline (Ex 8) with [(4,6-difluorophenyl)-pyridinato-N,C$^2$]$_2$IrCl dimer gave the desired product.

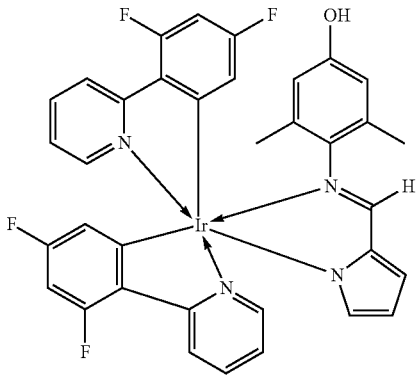

Example 15

According to General Method C above, reaction of 4-((1H-pyrrol-2-yl)methyleneamino)-3,5-dimethylphenol (Ex 9) with [(4,6-difluorophenyl)-pyridinato-N,C$^2$]$_2$IrCl dimer gave the desired product.

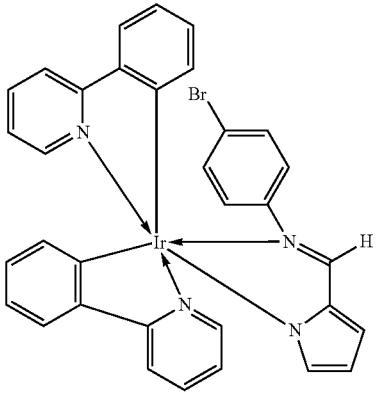

Example 16

According to General Method C above, reaction of N-((1H-pyrrol-2-yl)methylene)-4-bromoaniline (Ex 1) with [(phenylpyridinato-N,C²]₂IrCl dimer gave the desired product.

Example 17

According to General Method C above, reaction of 4-(2-((1H-pyrrol-2-yl)methyleneamino)ethyl)phenol (Ex 2) with [(phenylpyridinato-N,C²]₂IrCl dimer gave the desired product.

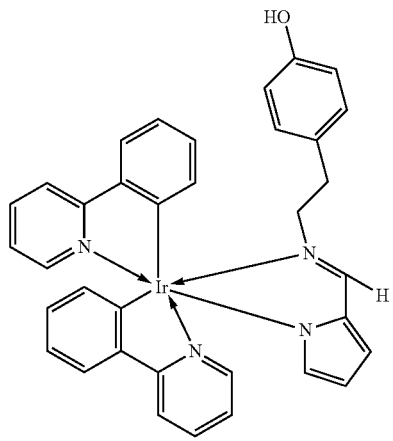

Example 18

According to General Method C above, reaction of N-((1H-pyrrol-2-yl)methylene)prop-2-en-1-amine (Ex 7) with [(phenylpyridinato-N,C²]₂IrCl dimer gave the desired product.

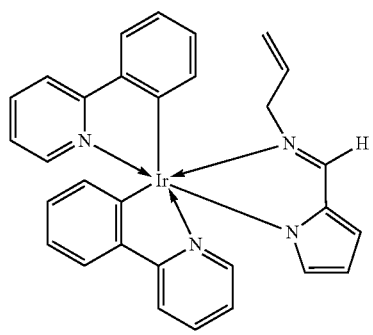

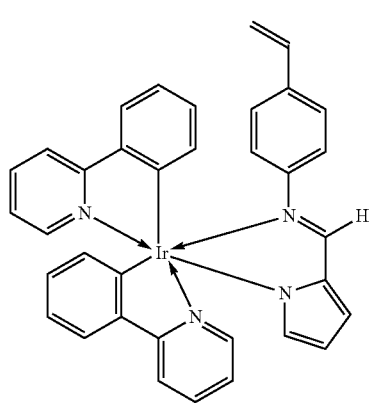

Example 19

According to General Method C above, reaction of N-((1H-pyrrol-2-yl)methylene)-4-vinylaniline (Ex 6) with [(phenylpyridinato-N,C²]₂IrCl dimer gave the desired product.

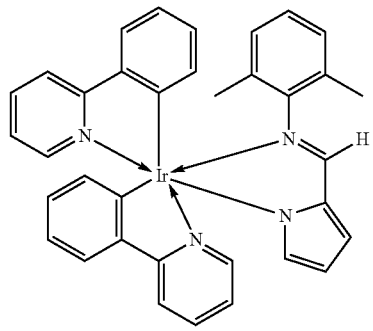

Example 20

According to General Method C above, reaction of N-((1H-pyrrol-2-yl)methylene)-2,6-di methylaniline (Ex 8) with [(phenylpyridinato-N,C²]₂IrCl dimer gave the desired product.

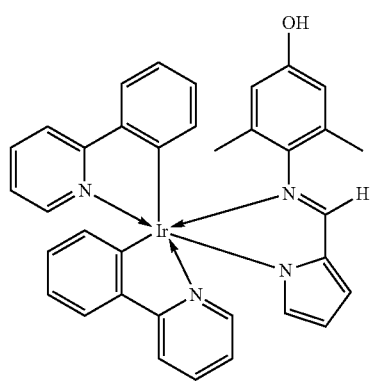

Example 21

According to General Method C above, reaction of 4-((1H-pyrrol-2-yl)methyleneamino)-3,5-dimethylphenol (Ex 9) with [(phenylpyridinato-N,C²]₂IrCl dimer gave the desired product.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An optoelectronic device having at least one layer comprising a polymer having pendant groups or end groups derived from at least one metal complex of formula IA

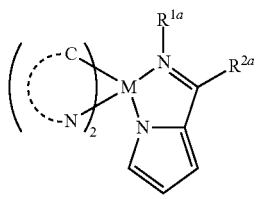

wherein
M is Ir, Co, or Rh;

is a cyclometallated ligand;
$R^{1a}$ is hydrogen, alkyl, substituted alkyl, aryl, substituted aryl, arylalkyl, or substituted arylalkyl,
$R^{2a}$ is hydrogen, alkyl, substituted alkyl, aryl, substituted aryl, arylalkyl, or substituted arylalkyl; and
at least one of $R^{1a}$ and $R^{2a}$ is substituted alkyl, substituted aryl, substituted arylalkyl, and at least one substitutent of the substituted alkyl, substituted aryl, or substituted arylalkyl is a polymerizable group.

2. An optoelectronic device according to claim 1, wherein at least one substitutent of the substituted alkyl, substituted aryl, or substituted arylalkyl is halo, hydroxy, alkoxysilyl, vinyl, or (meth)acrylate.

3. An optoelectronic device according to claim 1, wherein the polymer additionally comprises structural units derived from fluorene or substituted fluorene.

4. A polymer having structural or end units derived from a metal complex of formula IA

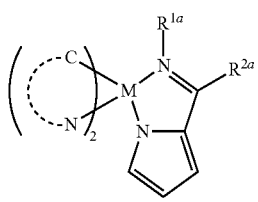

wherein
M is Ir, Co, or Rh;

is a cyclometallated ligand;
$R^{1a}$ is hydrogen, alkyl, substituted alkyl, aryl, substituted aryl, arylalkyl, or substituted arylalkyl,
$R^{2a}$ is hydrogen, alkyl, substituted alkyl, aryl, substituted aryl, arylalkyl, or substituted arylalkyl; and
at least one of $R^{1a}$ and $R^{2a}$ is substituted alkyl, substituted aryl, substituted arylalkyl, and at least one substitutent of the substituted alkyl, substituted aryl, or substituted arylalkyl is a polymerizable group.

5. A polymer according to claim 4, additionally comprising structural units derived from fluorene or substituted fluorene.

6. A polymer according to claim 4, wherein at least one substitutent of the substituted alkyl, substituted aryl, or substituted arylalkyl is halo, hydroxy, alkoxysilyl, vinyl, or (meth)acrylate.

7. A metal complex selected from

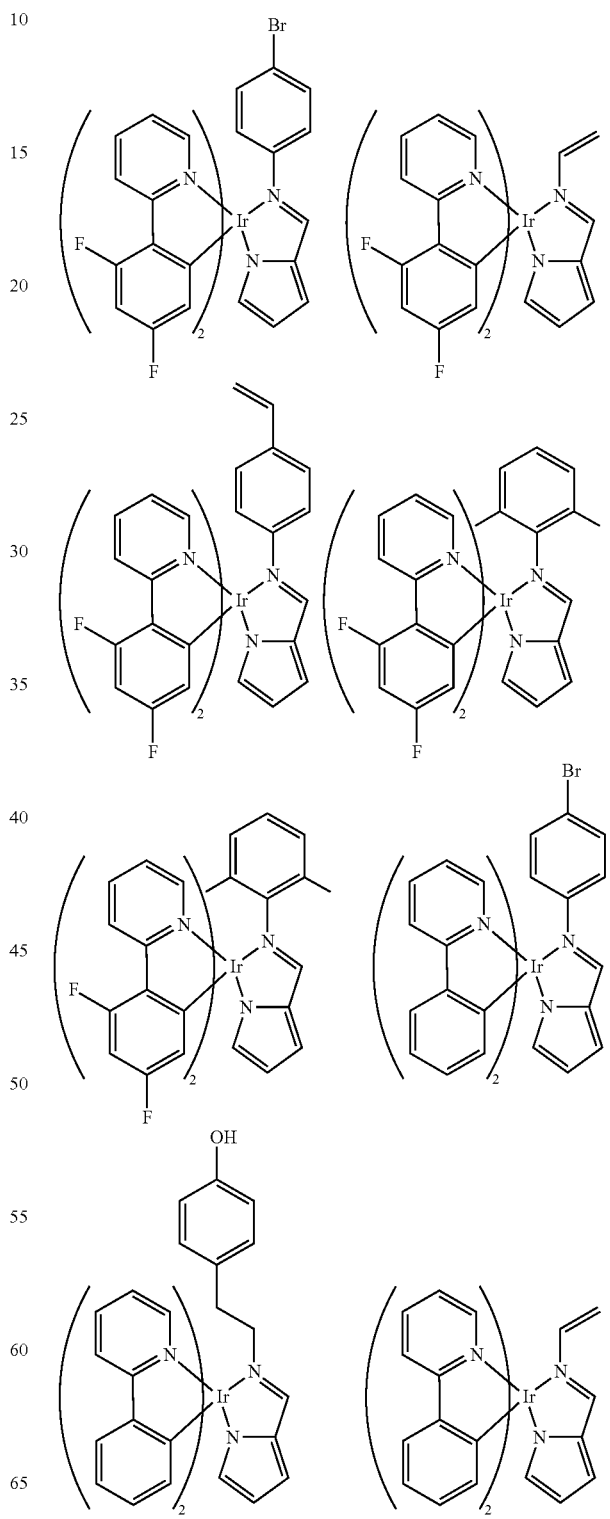

-continued
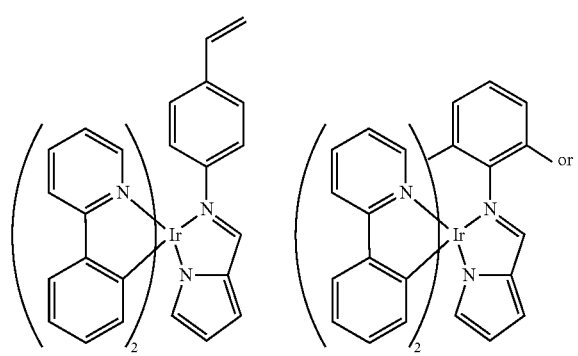
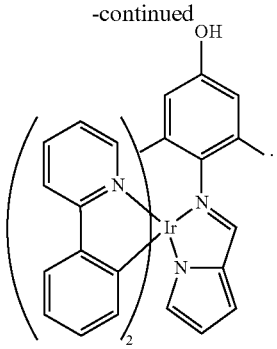
8. An optoelectronic device comprising a metal complex according to claim 7.
* * * * *

UNITED STATES PATENT AND TRADEMARK OFFICE
CERTIFICATE OF CORRECTION

| | | |
|---|---|---|
| PATENT NO. | : 7,989,580 B2 | Page 1 of 1 |
| APPLICATION NO. | : 12/260378 | |
| DATED | : August 2, 2011 | |
| INVENTOR(S) | : Litz et al. | |

It is certified that error appears in the above-identified patent and that said Letters Patent is hereby corrected as shown below:

On the Face Page, in Field (57), under "ABSTRACT", in Column 2, Line 19, delete "substitutent" and insert -- substituent --, therefor.

In Column 2, Line 56, delete "substitutent" and insert -- substituent --, therefor.

In Column 7, Line 25, delete "substitutent" and insert -- substituent --, therefor.

In Column 17, Line 28, in Claim 1, delete "substitutent" and insert -- substituent --, therefor.

In Column 17, Line 32, in Claim 2, delete "substitutent" and insert -- substituent --, therefor.

In Column 17, Line 65, in Claim 4, delete "substitutent" and insert -- substituent --, therefor.

In Column 18, Line 4, in Claim 6, delete "substitutent" and insert -- substituent --, therefor.

Signed and Sealed this
Fifth Day of June, 2012

David J. Kappos
*Director of the United States Patent and Trademark Office*